(12) United States Patent
Langford et al.

(10) Patent No.: US 10,058,345 B2
(45) Date of Patent: Aug. 28, 2018

(54) SINGLE-PASS ENDOSCOPIC VESSEL HARVESTING

(71) Applicant: TERUMO CARDIOVASCULAR SYSTEMS CORPORATION, Ann Arbor, MI (US)

(72) Inventors: Robert R. Langford, Eatonton, GA (US); Randal J. Kadykowski, South Lyon, MI (US); Kevin R. Line, Ann Arbor, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 328 days.

(21) Appl. No.: 14/926,305

(22) Filed: Oct. 29, 2015

(65) Prior Publication Data

US 2016/0045216 A1 Feb. 18, 2016

Related U.S. Application Data

(63) Continuation-in-part of application No. 14/021,537, filed on Sep. 9, 2013.
(Continued)

(51) Int. Cl.
*A61B 17/32* (2006.01)
*A61B 17/02* (2006.01)
(Continued)

(52) U.S. Cl.
CPC ........... *A61B 17/320016* (2013.01); *A61B 17/00008* (2013.01); *A61B 17/0218* (2013.01);
(Continued)

(58) Field of Classification Search
CPC ............ A61B 17/32; A61B 17/320016; A61B 17/320068; A61B 17/3205;
(Continued)

(56) References Cited

U.S. PATENT DOCUMENTS

| 5,013,312 A | 5/1991 | Parins et al. |
|---|---|---|
| 5,810,806 A | 9/1998 | Ritchart |

(Continued)

OTHER PUBLICATIONS

Souza, Domingos S.R., et al., The no-touch technique of harvesting the saphenous vein for coronary artery bypass grafting surgery, Multimedia Manual of Cardiothoracic Surgery, 1-6, 2008.
(Continued)

*Primary Examiner* — Todd Scherbel
(74) *Attorney, Agent, or Firm* — Darryl Newell; MacMillan, Sobanski & Todd, LLC

(57) ABSTRACT

An endoscopic harvesting device removes a vessel from a body. The vessel has an anterior side closest to the skin. A sheath extends in a longitudinal direction with a dissector tip for advancing along the vessel substantially along the anterior side to create a flanking tunnel spaced away from the vessel. A ring-shaped blade is mounted to the sheath and is disposed in a plane substantially perpendicular to the longitudinal direction and proximal of the dissector tip. The blade forms a lateral loop to encircle the vessel from the flanking tunnel. The blade comprises an inductively-heated ferromagnetic member configured to make a vasiform cut including a pedicle around the vessel as the sheath advances.

16 Claims, 8 Drawing Sheets

Related U.S. Application Data

(60) Provisional application No. 62/201,338, filed on Aug. 5, 2015.

(51) Int. Cl.

| | | |
|---|---|---|
| *A61B 18/08* | (2006.01) | |
| *A61B 17/00* | (2006.01) | |
| *A61B 18/14* | (2006.01) | |
| *A61F 2/06* | (2013.01) | |
| *A61B 18/00* | (2006.01) | |

(52) U.S. Cl.
CPC .... *A61B 17/320068* (2013.01); *A61B 18/082* (2013.01); *A61B 18/1477* (2013.01); *A61B 2017/00778* (2013.01); *A61B 2017/00969* (2013.01); *A61B 2017/320072* (2013.01); *A61B 2017/320078* (2017.08); *A61B 2018/00595* (2013.01); *A61B 2018/00601* (2013.01); *A61B 2018/1407* (2013.01); *A61F 2/062* (2013.01)

(58) Field of Classification Search
CPC .......... A61B 17/32053; A61B 17/3209; A61B 17/322; A61B 2017/320064; A61B 2017/320072; A61B 2017/320076
See application file for complete search history.

(56) References Cited

U.S. PATENT DOCUMENTS

| | | | |
|---|---|---|---|
| RE36,043 | E | 1/1999 | Knighton |
| 5,916,233 | A | 6/1999 | Chin |
| 5,976,168 | A | 11/1999 | Chin |
| 5,980,549 | A | 11/1999 | Chin |
| 6,129,661 | A | 10/2000 | Iafrati et al. |
| 6,309,400 | B2 | 10/2001 | Beaupre |
| 6,527,771 | B1 | 3/2003 | Weadock et al. |
| 7,077,803 | B2 | 7/2006 | Kasahara et al. |
| 7,331,971 | B2 | 2/2008 | Kasahara et al. |
| 7,601,125 | B1 | 10/2009 | Kai |
| 7,909,762 | B2 | 3/2011 | Usher et al. |
| 7,942,891 | B2 | 5/2011 | Genovesi et al. |
| 7,981,133 | B2 | 7/2011 | Chin |
| 8,097,010 | B2 | 1/2012 | Kasahara et al. |
| 8,292,879 | B2 | 10/2012 | Manwaring et al. |
| 8,372,096 | B2 | 2/2013 | Kadykowski et al. |
| 8,430,898 | B2 | 4/2013 | Wiener et al. |
| 2005/0192613 | A1* | 9/2005 | Lindsay .......... A61B 17/00008 606/190 |
| 2006/0217706 | A1 | 9/2006 | Lau |
| 2008/0208192 | A1 | 8/2008 | Kadykowski et al. |
| 2008/0255407 | A1 | 10/2008 | Blakeney et al. |
| 2010/0268205 | A1 | 10/2010 | Manwaring |
| 2010/0292533 | A1 | 11/2010 | Kasahara et al. |
| 2015/0073207 | A1 | 3/2015 | Langford |

OTHER PUBLICATIONS

Practical Induction Heat Treating (#06098G), Chapter 2—Theory of Heating by Induction, 5-10, 2001, ASM.

Domingos S.R. Souza, et al., Improved patency in vein grafts harvested with surrounding tissue: results of a randomized study using three harvesting techniques, The Annals of Thoracic Surgery, Ann Thorac Surg 2002;73:1189-1195, Feb. 7, 2010.

Ron Kurtus, Classifications of Magnetic Materials, revised Mar. 23, 2012, at http://www.school-for-champions.com/science/magnetic_materials.htm#.V3Hkp_krJhE.

Stedman's Medical Dictionary, 218, 1982, Williams & Wilkins, Baltimore, MD, USA.

Isao Takeuchi, Observation of Capillary Network in Gastric Mucosa with Biopsy Specimen—Mucosal Redness Found by Gastroendoscopical Examination and the Structure of Capillaries, Gastroenterological Endoscopy, 957-967, vol. 28(5), May 1986.

\* cited by examiner

SINGLE-PASS ENDOSCOPIC VESSEL HARVESTING

CROSS REFERENCE TO RELATED APPLICATIONS

This application is a continuation-in-part of U.S. Ser. No. 14/021,537, filed Sep. 9, 2013, entitled "Single-Pass Endoscopic Vessel Harvesting," and claims priority from U.S. provisional application Ser. No. 62/201,338, filed Aug. 5, 2015, entitled "Vessel Cauterizing Ring."

STATEMENT REGARDING FEDERALLY SPONSORED RESEARCH

Not Applicable.

BACKGROUND OF THE INVENTION

The present invention relates in general to harvesting of living vessels for use in grafting, and, more specifically, to a harvesting device for endoscopically removing a vessel in a "no touch" condition with surrounding pedicle of fat and connective tissue.

Blood vessels are often dissected from one portion of a living body to be implanted in another portion of the body by a surgical procedure, such as in a coronary artery bypass graft (CABG) or other cardiovascular procedure. An artery or vein is "harvested" (i.e., removed) from its natural location in a patient's body and reconnected to provide blood circulation elsewhere in the body. Among the preferred sources for the vessels to be used as the bypass graft are the saphenous vein in the leg and the radial artery in the arm.

Endoscopic surgical procedures for harvesting a section of a blood vessel (e.g., the saphenous vein) subcutaneously have been developed in order to avoid disadvantages and potential complications of harvesting of the blood vessel by exposing the desired vein section externally through a continuous incision along the leg. The continuous incision for exposing the vein and for introducing the surgical instruments to seal and sever adjoining tissue and side branches of the vessel results in a significant healing process and associated risks.

The known minimally-invasive endoscopic techniques employ a small incision for locating the desired vessel and for introducing one or more endoscopic devices into the small incision. For example, typical commercially available products for performing the endoscopic blood vessel harvesting procedure include a number of separate endoscopic devices that are each inserted into the patient. These endoscopic devices include, for example, an insufflation mechanism having plastic tubing to supply air or $CO_2$ to insufflate the subcutaneous area; an endoscope having a camera and light cables in order to visualize both the dissection and harvesting procedures; a dissector mechanism to dissect or separate the vessel from connective tissues in the body (i.e., skeletonizing the vessel); and a cutting mechanism to sever and seal any side branches from the vessel so that the vessel can be removed from the body. In certain instances, the combination of mechanisms can be bulky and cumbersome for the clinician performing the vessel harvesting. Also, in certain instances, these mechanisms require that a relatively large diameter wound and cavity be formed within the patient in order to accommodate all the separate mechanisms.

Existing harvesting devices have required an intricate and physically demanding procedure to isolate a vessel from surrounding tissue and to cut and coagulate side branches. This required a high level of skill and practice for the person performing the harvesting procedure. Even with good expertise, several potential sources of damage to the harvested vessel remain. Harvesting typically requires multiple passes of one or more separate devices resulting in much contact with the vessel, potentially leading to endothelial damage. To create a sufficient working space and to allow visualization for tissue separation and side branch cutting, significant insufflation is often used. The $CO_2$ insufflation gas can lead to tissue acidosis, $CO_2$ embolism, and other complications. The common use of electrocauterization for cutting and coagulating the side branches can result in thermal spreading to the harvested vessel and sometimes also results in side branch stubs that are too short for obtaining a good, leak-proof seal.

It has been discovered that improved patency can be obtained for a vein graft if some surrounding tissue is left intact around the desired vessel. However, conventional endoscopic devices have not been capable of maintaining a layer of surrounding tissue over the harvested vessel.

SUMMARY OF THE INVENTION

The present invention provides a user-friendly device and procedure for endoscopically harvesting a vessel with a surrounding pedicle for use in grafting. Patency of the vessel is improved and trauma is reduced as a result of harvesting with no direct contact with the vessel. The simplified device and procedure achieve successful harvesting with less need for training or specialized skills.

In one aspect of the invention, an apparatus is provided for endoscopic harvesting of a vessel from a body. The vessel has an anterior side closest to the skin. A sheath extends in a longitudinal direction with a dissector tip for advancing along the vessel substantially along the anterior side to create a flanking tunnel spaced away from the vessel. A ring-shaped blade is mounted to the sheath and is disposed in a plane substantially perpendicular to the longitudinal direction and proximal of the dissector tip. The blade forms a lateral loop to encircle the vessel from the flanking tunnel. The blade comprises an inductively-heated ferromagnetic member configured to make a vasiform cut including a pedicle around the vessel as the sheath advances.

DETAILED DESCRIPTION OF PREFERRED EMBODIMENTS

Figure 1:
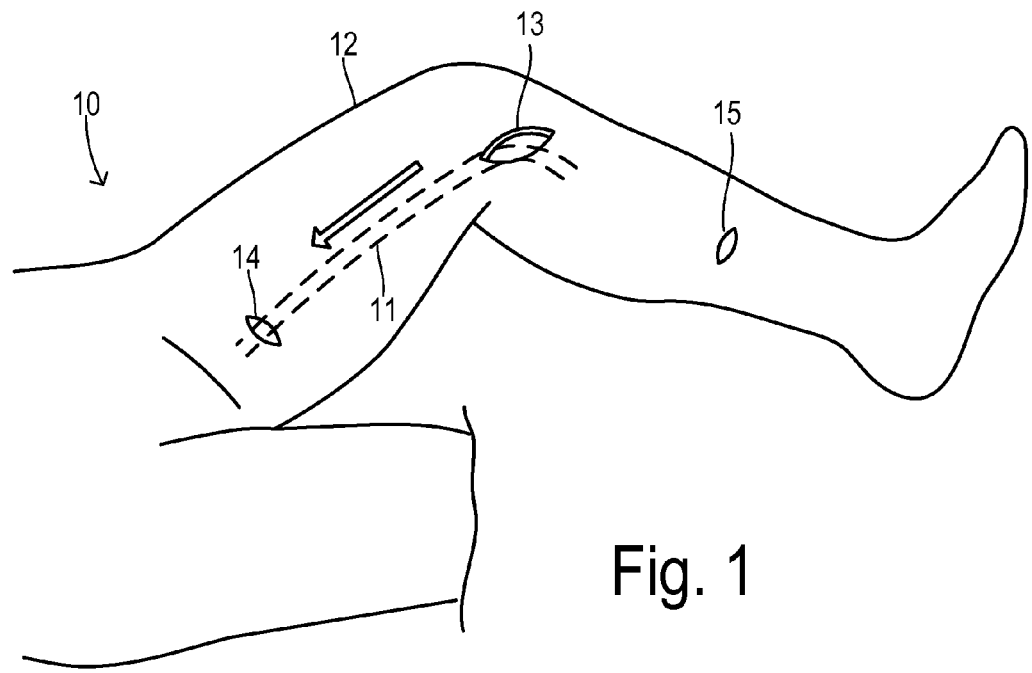
FIG. 1 is an external view of a saphenous vein being harvested from a leg.

Referring now to FIG. 1, a patient 10 has a saphenous vein 11 within a lower limb 12. An incision 13 is made directly above vein 11, and tissue is peeled back from incision 13 to access the vein. Endoscopic instruments have been inserted through incision 13 to separate vein 11 from connective tissue and then to sever and cauterize side branches that extend from vein 11. A second incision or stab wound 14 is created at a second position on limb 12 so that a second end of vein 11 can be severed. Vein 11 is then extracted through one of the incisions. The entry point or second incision can be placed at various locations along vein 11 as shown at 15.

Figure 2:
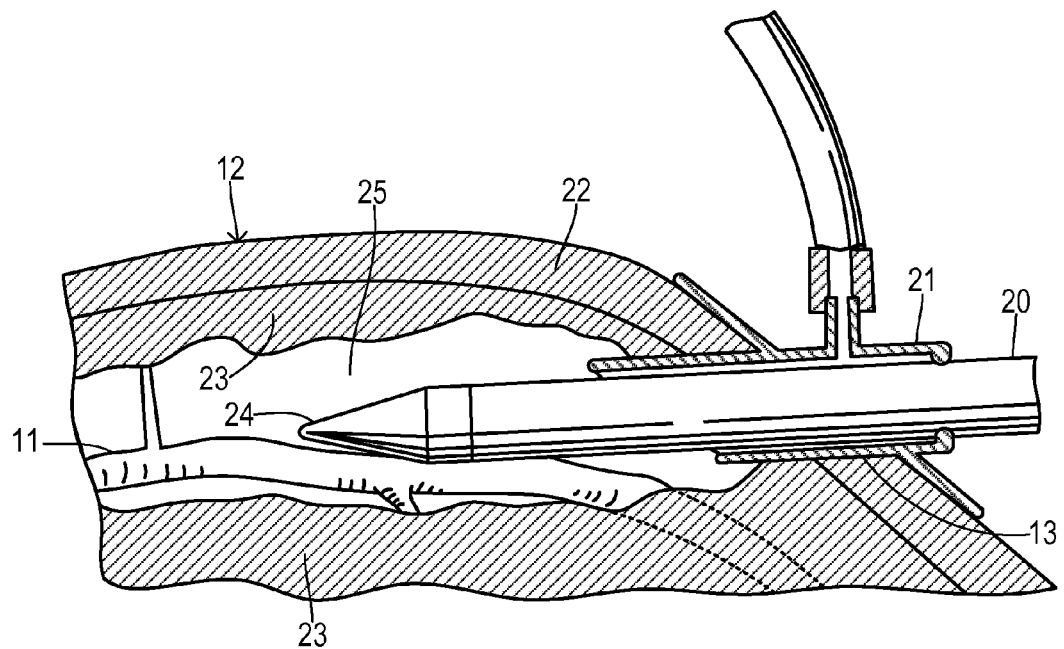
FIG. 2 shows a prior art dissector isolating a saphenous vein in an endoscopic procedure.

FIG. 2 shows a prior art dissector rod 20 inserted into a body through a trocar 21 which maintains an opening at incision 13 and provides a seal for insufflation gas. Trocar 21 may be adhesively attached to skin 22. Subcutaneous tissue 23 is peeled opened using a transparent tip 24 on dissector rod 20 to create an interior cavity 25 around saphenous vein 11. Insufflation gas may be introduced into cavity 25 (e.g., via appropriate tubing to trocar 21 or via a channel within rod 20) in order to maintain visualization of vein 11 via an endoscopic camera provided within dissector 20 as is known in the art. Dissector rod 20 may be removed after exposing vein 11 so that a cutting instrument can be reinserted for cutting and coagulating the side branches. By the time the section of vein 11 is removed, it has been subjected to handling that potentially causes endothelial and/or thermal injury.

Figure 3:
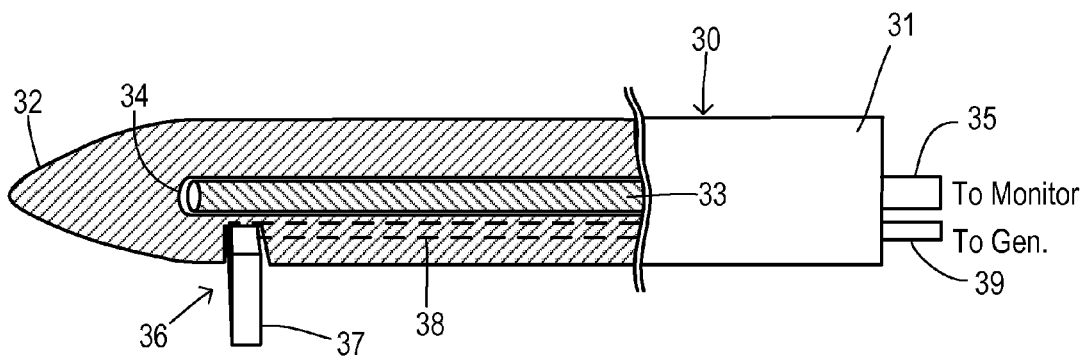
FIG. 3 is a partial cross section showing one embodiment of a harvesting device of the invention.

An improved endoscopic surgical instrument for harvesting a vessel in a single pass and with an intact pedicle around the vessel is shown in FIG. 3. A device body (i.e., a rod or sheath) 30 has a handle 31 at one end and a dissector tip 32 at the other end. An endoscope element 33 is contained within a receptacle 34 within sheath 30 having a forward view through tip 32 (i.e., at least a portion of tip 32 is preferably made of a transparent material). Endoscope element 33 has an end connection 35 connected to a monitor and light source as is known in the art.

A cutter element 36 assembles into a corresponding groove(s) on sheath 30. Element 36 has an intermediate section 38 connected at one end to a cutting blade 37 which is positioned proximally of tip 32. Blade 37 is disposed in a plane substantially perpendicular to the longitudinal direction of sheath 30, and is the only ultrasonically-active portion of cutter element 36. At the other end of intermediate section 38, a connector 39 is provided for coupling to a power source which may preferably be an ultrasonic generator, for example. Other energy sources could also be used. Intermediate section 38 nests together with sheath body 30 in order to provide a generally smooth outer surface of the combined instrument. Preferably, no insufflation port is constructed in the harvester since no $CO_2$ insufflation is necessary.

Figure 4:
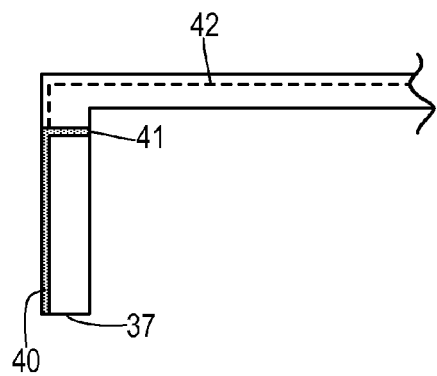
FIG. 4 is a side view of a blade member.
Figure 5:
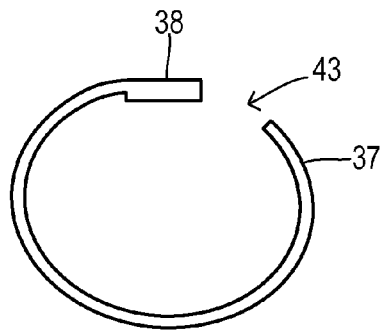
FIG. 5 is an end view of a blade member.

Blade 37 is ring-shaped and may perform any type of cutting, such as electro-cautery, ultrasonic, or ferromagnetic. In one preferred embodiment, ultrasonic cutting and cauterization may be used. As shown in FIG. 4, ring-shaped blade 37 may have a leading edge 40 and a terminal edge 41 made of a piezoelectric material of the type conventionally used in ultrasonic surgical instruments. Signal transmission lines 42 are preferably disposed on intermediate element 38 to couple a desired oscillating signal to the piezoelectric material when cutting is to be performed. By avoiding the generation of any significant heat, thermal spreading to the target vessel is avoided. As shown in the end view of FIG. 5, blade 37 preferably forms an incomplete ring resulting in a gap 43 between terminal end 41 and intermediate section 38. The ring is not complete around the circumference so that the vessel can be loaded within the ring as a first step, resulting in the vessel and surrounding pedicle being centered in the ring. Then the ring and its support/power supply section can be attached to the harvester rod, forming one integral piece that can be manually guided to dissect the vessel/pedicle.

Figure 6:
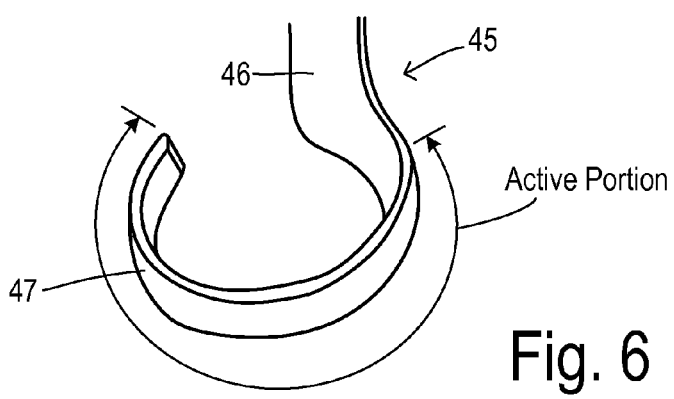
FIG. 6 is a perspective view of a blade member.

FIG. 6 illustrates another embodiment of a ring-shaped blade 45 having an intermediate section 46 transitioning to a curved end 47. Only curved end 47 is ultrasonically active. Preferably, a variety of sizes and shapes are made available to the user in order to adapt an instrument to the size and/or location of a target vessel being harvested from a particular patient.

Figure 7:
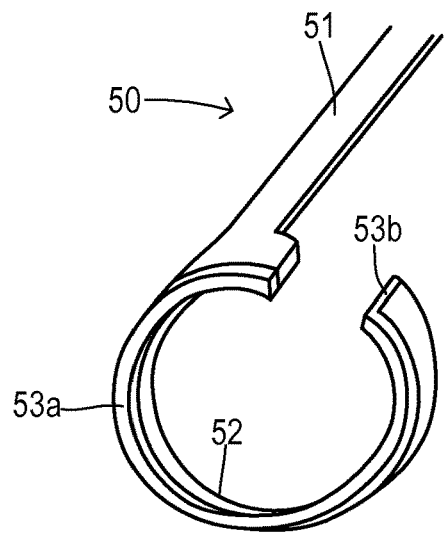
FIG. 7 is a perspective view of another blade member.

FIG. 7 shows yet another embodiment of a cutting element 50 having an intermediate section 51 supporting a ring blade 52. A narrow leading edge of ring blade 52 is comprised of an ultrasonic material 53A, while an open end 53B likewise contains the ultrasonic material for performing tissue cutting during initial placement of ring blade 52 around a vessel as described below. Active areas 53A and 53B can alternatively be comprised of ferromagnetic material for cutting and cauterizing tissue using heat induced by an appropriate signal conductor arranged to generate an alternating magnetic field within the ferromagnetic material.

Figure 8:
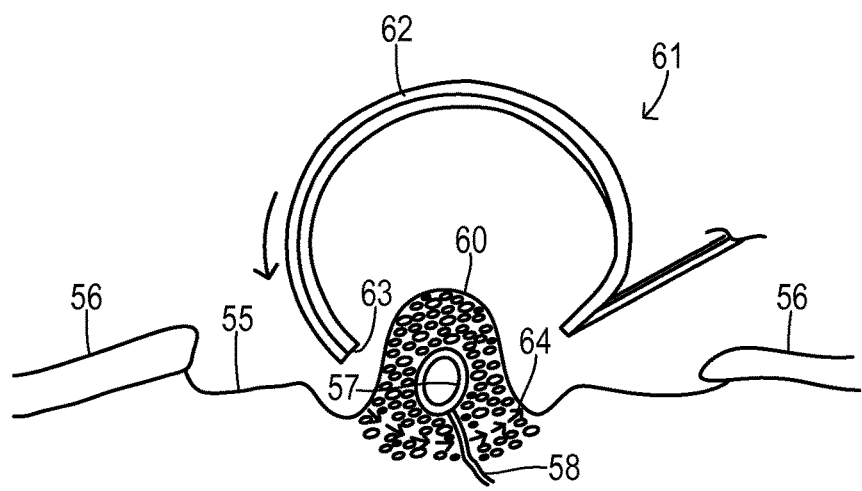
FIG. 8 depicts a blade ring about to be put in place around a vessel at an initial incision.

As shown in FIG. 8, an incision has been made through a skin layer 56 to internal tissue 55 in order to obtain access to a tissue region 60 around a target vessel 57. An anterior side of vessel 57 (i.e., toward the exterior or skin side) is mostly free of side branches. Thus, a side branch 58 extends deeper into tissue 55 away from the anterior side. A cutting element 61 has a ring blade 62 with an open end 63 which is used to cut beneath target vessel 57 so that ring blade 62 may be placed as a lateral loop encircling vessel 57. Tissue 60 around vessel 57 is preferably pinched upward with a grasping tool (not shown) in order to facilitate entry of open end 63 along an incision path 64. Initial placement of ring blade 62 into path 64 may be done prior to or after the installation of cutting element 61 onto the sheath body.

Figure 9:
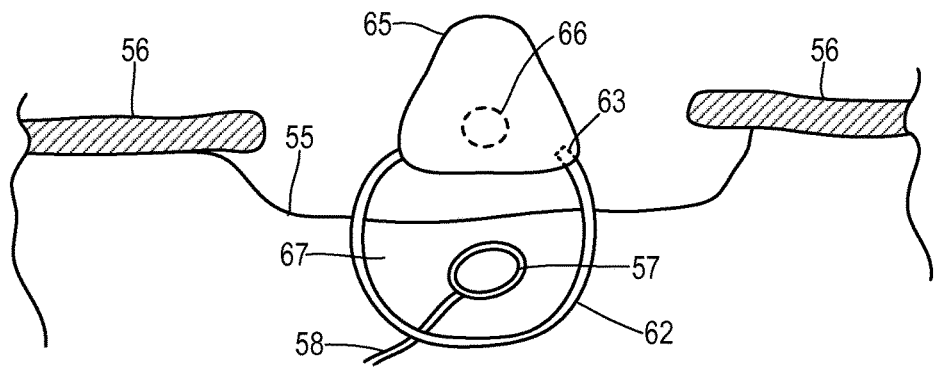
FIG. 9 depicts the blade ring after inserting it around a vessel at the initial incision and ready to make a vasiform cut.

FIG. 9 shows ring blade 62 in its initial position around target vessel 57 with ring blade 62 installed onto dissector tip 65. An endoscope lens 66 incorporated in tip 65 may be used to visualize the tissue around and including target vessel 57. A tissue section 67 within the perimeter of ring blade 62 makes up a pedicle around vessel 57. With the device in the initial position shown in FIG. 9, vessel 57 remains fully intact (i.e., its end has not yet been cut). By maintaining the integrity of vessel 57 and its surrounding pedicle 67 when blade 62 is advanced, a counter-traction is maintained when tip 65 performs its cutting action along vessel 57 as described below.

Once cutting element 61 is assembled onto the sheath body, open end 63 of blade 62 is preferably positioned in an open space inside the general profile of the sheath body. This ensures that all the tissue to be cut is contacted by the active region of the ring. Open end 63 does not actually contact tip 65, but is instead free to vibrate ultrasonically in response to the energy source.

Figure 10:
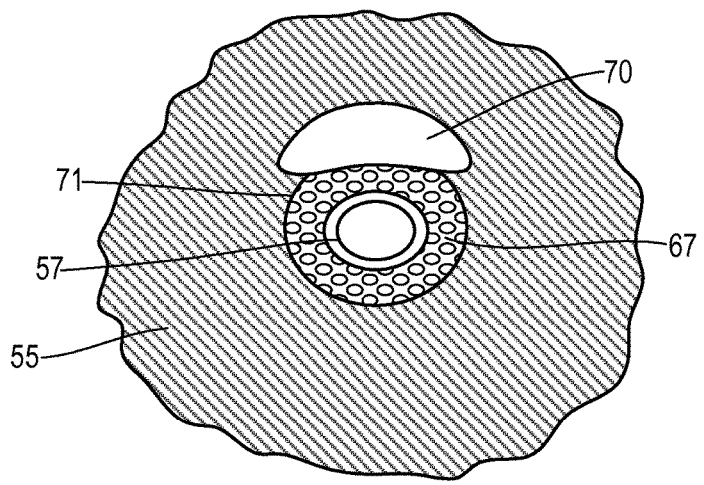
FIG. 10 is a cross-sectional, subcutaneous view showing a harvested vessel with surrounding pedicle and flanking tunnel during harvesting.
Figure 11:
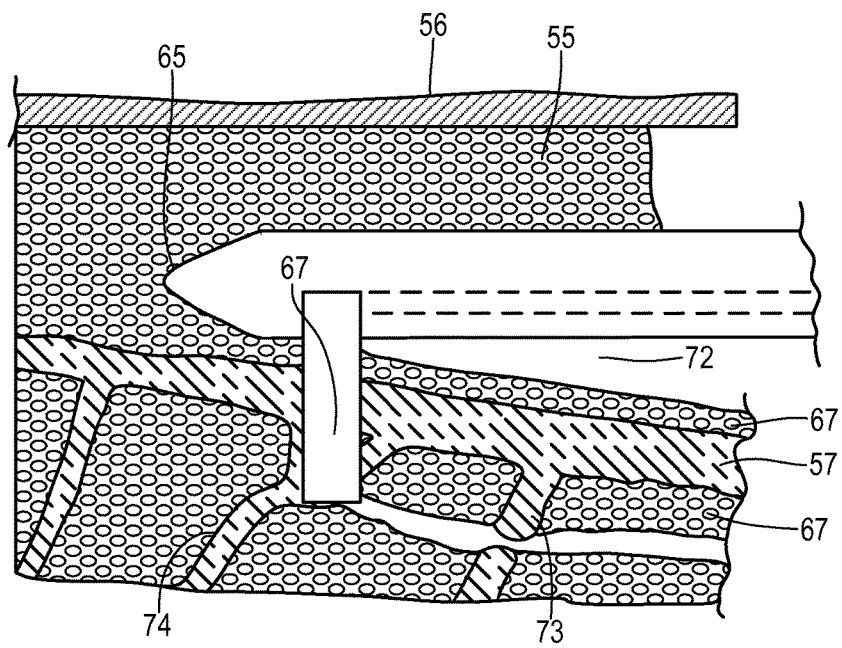
FIG. 11 is a longitudinal cross section showing the harvesting of a vessel according to the present invention.

With ring blade 62 encircling target vessel 57 at the initial incision, dissector tip 65 is advanced along the vessel substantially along the anterior side in order to create a flanking tunnel 70 spaced away from vessel 57 as shown in FIG. 10. As an operator presses the handle forward and guides dissector tip 65 just slightly above the position of target vessel 57, a vasiform cut 71 is made encircling a pedicle 67 and vessel 57. The length of vasiform cut 71 progresses as dissector tip advances for a desired length of vessel to be harvested. FIG. 11 shows a side view during the formation of a vasiform cut around target vessel 57. As the operator advances tip 65 above target vessel 57 so as to maintain an amount of connective tissue 55 between tip 65 and vessel 57, ring blade 62 is energized in order to make the vasiform cut that simultaneously excises pedicle 67 and vessel 57 while automatically severing and cauterizing side branches such as branches 73 and 74. Thus, only a single pass is needed in order to form the desired pedicle with embedded vessel, thereby resulting in minimal disturbance or injury to target vessel 57.

Figure 12:
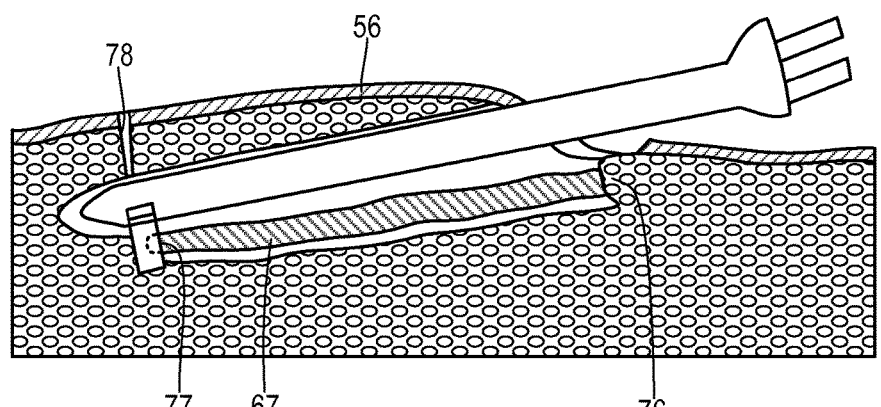
FIG. 12 illustrates a dissected pedicle ready for extraction from the body.

As shown in FIG. 12, once a sufficient length of pedicle 67 containing the target vessel has been made between an initial end 76 and a final end 77, a second incision 78 is made through skin 56 in order to access final end 77. A scalpel or other cutting instrument can then be used at each incision in order to sever the ends of pedicle 67 so that the harvested vessel can be removed and the remaining ends of the saphenous vein can be sealed off. Thereafter, instrument 30 may be removed from the patient.

Figure 13:
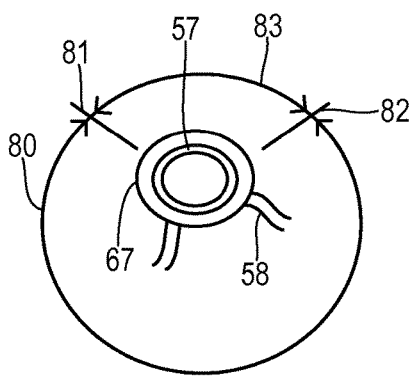
FIG. 13 is a cross section of a vessel illustrating the typical locations of side branches.
Figure 14:
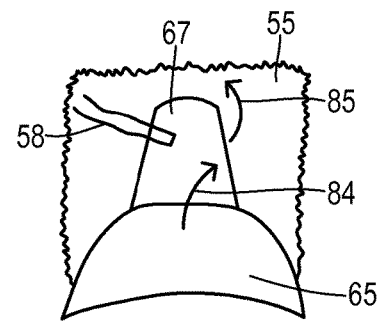
FIG. 14 illustrates a turning maneuver for severing and cauterizing a side branch being encountered near an anterior side of the harvested vessel.

FIG. 13 shows a transverse cross-section through vessel 57 and pedicle 67. An anterior side 83 of vessel 57 is located between radial positions 81 and 82. This anterior side 83 is generally free from side branches. Nearly all the side branches, such as side branch 58, are encountered at a non-anterior side 80 between radial positions 81 and 82. By configuring the ring blade to span non-anterior portion 80 and to have each end of the ring contained within the flanking tunnel, a procedure is obtained wherein most all side branches are automatically cut and cauterized without the operator taking any special actions. In the event that a side branch is encountered along the anterior side as shown in FIG. 14, the operator may rotate tip 65 in a direction away from a side branch 58 as shown by arrow 84 in order to avoid contact between dissector tip 65 and branch 58. This places branch 58 in a position to be cut by the ring blade. As tip 65 advances past the position of side branch 58, the operator restores the handle to the original orientation, thus bringing tip 65 back to the original anterior side as shown by arrow 85.

Figure 15:
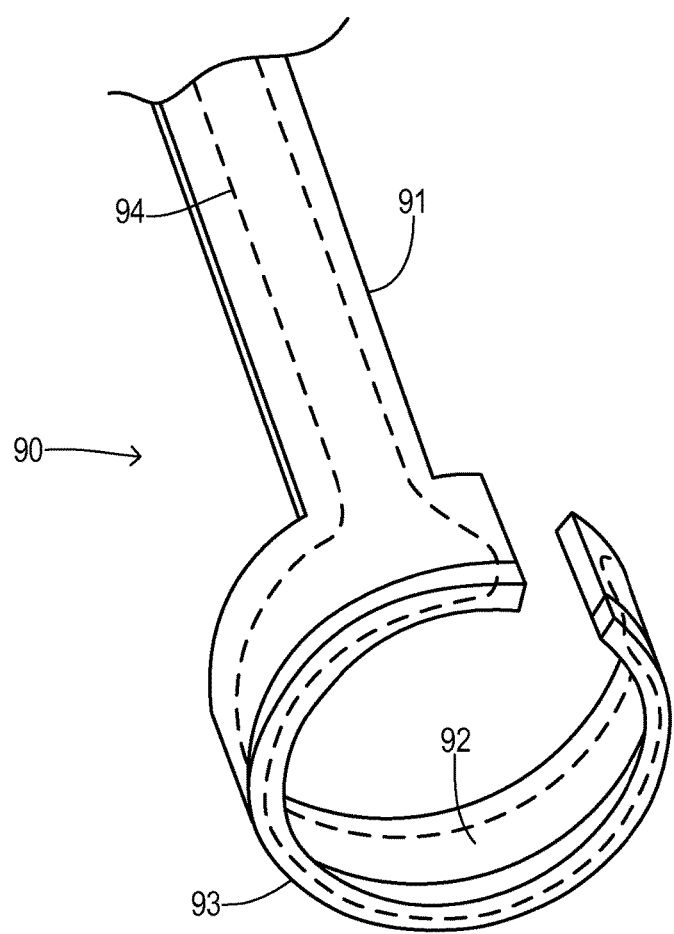
FIG. 15 is a perspective view of a ring-blade having a leading edge carrying a ferromagnetic member and a signal conductor for inducing heating of the member.

FIG. 15 shows a cutting element 90 having an intermediate section 91 supporting a ring blade 92. A ferromagnetic member 93 is disposed at a leading edge blade 92. A conductor loop 94 is incorporated into cutting element 90 and includes a portion that is disposed alongside ferromagnetic member 93 in order to couple an alternating magnetic field surrounding loop 94 that is induced by an alternating current signal from a generator (not shown). Ferromagnetic member 93 induces heating as known in the art, and as shown for example in U.S. Pat. No. 8,292,879. Selection of an appropriate ferromagnetic material for member 93 and the parameters of an alternating signal (e.g., frequency) provided by the signal generator may be as shown in U.S. Pat. No. 8,292,879.

Figure 16:
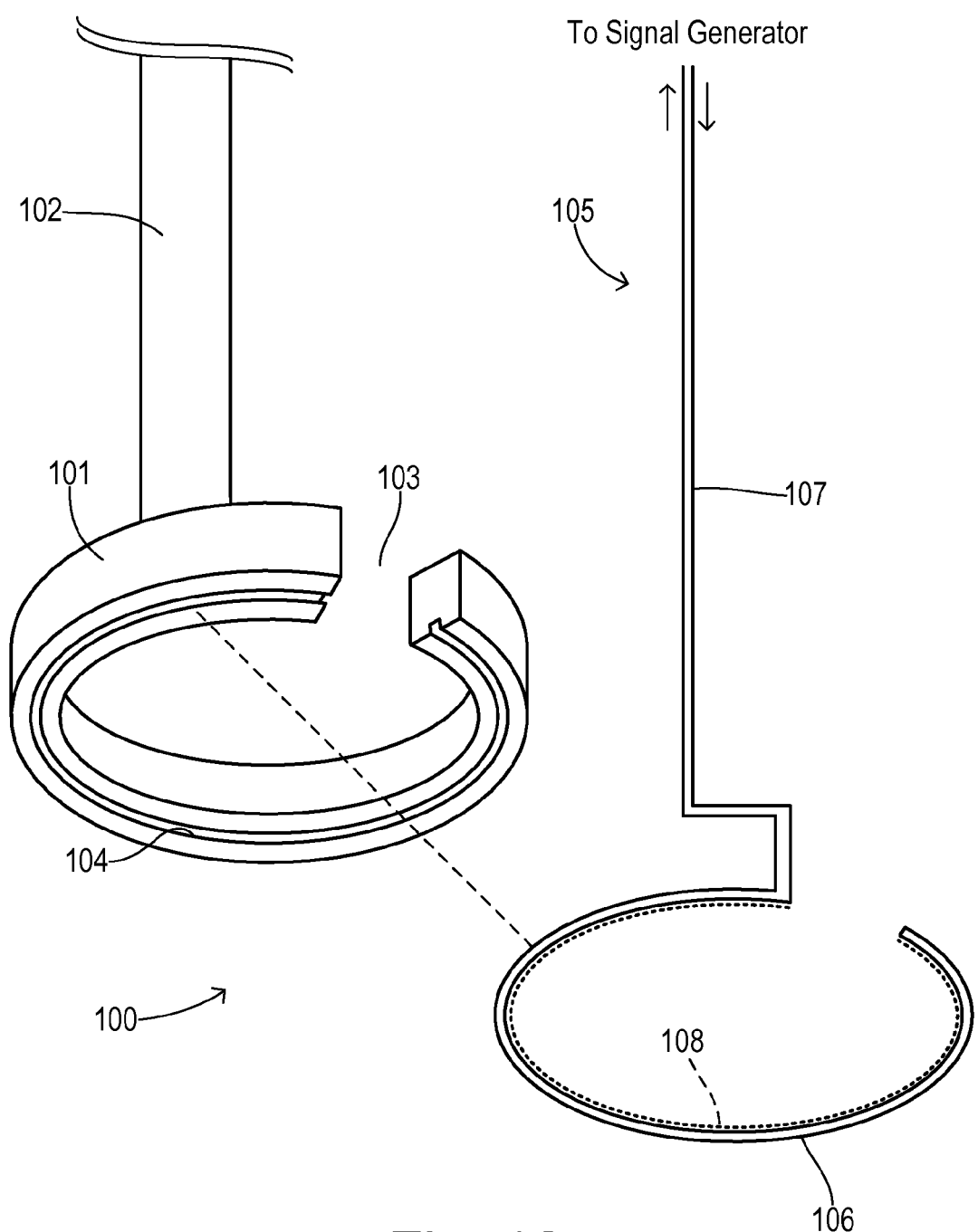
FIG. 16 is a perspective view of another embodiment of a ferromagnetic ring-blade wherein the ferromagnetic member is comprised of a coating applied to a conductor loop.

FIG. 16 shows another embodiment of a cutting element 100 having a base 101 supported by a rod 102. Base 101 is formed as a truncated ring with a gap 103 and has a recessed slot 104 sunk into its surface along a leading edge. A ferromagnetic member 105 is comprised of a conductor forming a loop 106 at one end which is connected to a signal generator (not shown) via a lead-in section 107. Loop 106 is received in slot 104, and rod 102 may have a longitudinal slot (not shown) for receiving lead-in section 107. To provide induction heating at the leading edge, appropriate regions of loop 106 are coated with a ferromagnetic material (e.g., a coating 108 applied circumferentially over a section of the wire along one of its passes within loop 106). Alternatively, base 101 can incorporate the ferromagnetic material.

Figure 17:
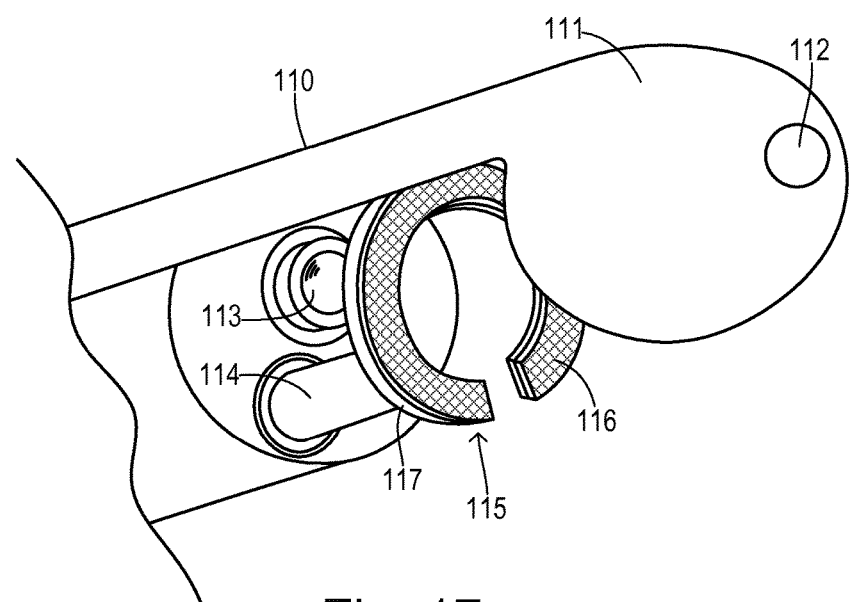
FIGS. 17 and 18 are perspective views of ring-blades with ferromagnetic members that pivotably extend from a harvester rod, shown in retracted and extended positions, respectively.

FIG. 17 shows a harvester rod 110 having a distal tip 111 with a curved or pointed surface adapted to penetrate connective tissue, for example. A transparent window 112 is aligned with an endoscope 113 mounted in rod 110 as known in the art. A cutter support shaft 114 extends through rod 110 and is pivotable around its longitudinal axis using a control mechanism in a handle as known in the art. A ring blade 115 is attached to the end of shaft 114 and includes a ferromagnetic member 116 on a leading surface in order to make a vasiform cut as described above. Ferromagnetic member 116 may be comprised of a block of desired material, and an appropriate conductor may be disposed within a base layer 117, for example. By rotating shaft 114, blade 115 can be shifted between a retracted position behind distal tip 111 (as shown) and an extended position where blade 115 can make the vasiform cut.

Figure 18:
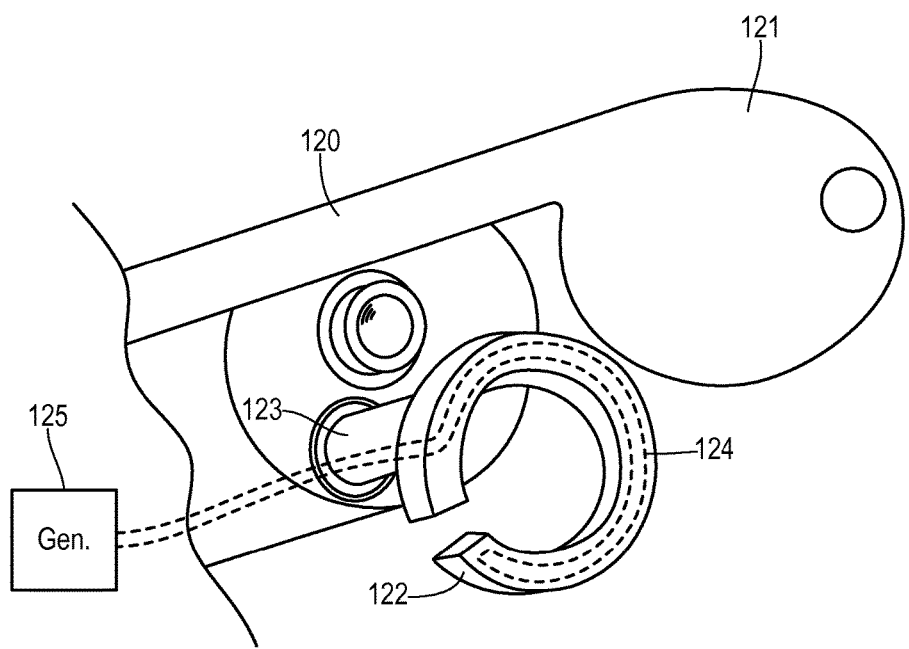

FIG. 18 shows a similar embodiment of a harvester rod 120 with a distal tip 121 and a ring blade 122 mounted to a pivotable shaft 123. Blade 122 is shown with shaft 123 rotated to place blade 122 in an extended position. In this embodiment, ferromagnetic member 124 may be comprised of a conductor loop embedded in or disposed on a surface of ring blade 122. Member 124 is comprised of a conductive loop with a coating of ferromagnetic material selectively placed on the conductor along a leading edge of blade 122. The conductor extends to a signal generator 125 which supplies an alternating signal for inducing heating of the ferromagnetic material.

Using the foregoing invention, a target vessel can be gently retracted and may be harvested together with a surrounding pedicle that provides protection and life support for the vessel. No $CO_2$ is needed, although a small amount of $CO_2$ insufflation may be used if desired, but may be performed at a significantly reduced amount as compared to the prior art. A speed of forward movement of the dissector tip and ring blade may be adjusted by the operator according to any variations in the tissue as they advance. In addition, a magnitude and/or frequency of the alternating signal can be adjusted by the operator to varying the induced temperature in the ferromagnetic member in order to ensure adequate coagulation and ligation of a range of small to larger side branches. A passive or low suction incorporated in the harvester could also be used in order to remove any desiccation fluid created by the ring activity plus any smoke that may need to be vented. At no point in the inventive procedure is the vessel "skeletonized". The anterior pass of the dissector tip is steered so that several cell layers of fat and connective tissue remain attached to the vessel. Visualization of the vessel through the thin layers is sufficient to steer the instrument and anticipate the vessel's path.

What is claimed is:

1. Apparatus for endoscopic harvesting of a vessel from a body, wherein the vessel has an anterior side closest to a skin of the body, comprising:
   a sheath extending in a longitudinal direction and terminating in a tapered dissector tip for advancing along the vessel substantially along the anterior side to create a flanking tunnel spaced away from the vessel; and
   a ring-shaped blade mounted to the sheath and disposed in a plane substantially perpendicular to the longitudinal direction and proximal of the dissector tip, wherein the blade forms a lateral loop having a partial ring with a terminal end, wherein the blade and sheath have a first configuration in which the terminal end pierces tissue around the vessel in order to center the vessel and a surrounding pedicle within the blade without cutting the vessel, wherein the blade and sheath have a second configuration in which the terminal end fits within a profile of the sheath so that the partial ring and the sheath completely encircle the vessel from the flanking tunnel, and wherein the blade comprises an active leading edge configured to make a vasiform cut including a pedicle around the vessel as the sheath advances and the vessel remains unsevered while the vasiform cut is made.

2. The apparatus of claim 1 wherein the vessel has a plurality of side branches, and wherein the active leading edge cuts and cauterizes the side branches as the sheath advances.

3. The apparatus of claim 1 wherein the blade is rotationally mounted to the sheath for pivoting between a retracted position and an extended position.

4. The apparatus of claim 1 wherein a gap in the partial ring adjacent the terminal end provides entry into the partial ring while in the first configuration, and wherein the terminal end pierces the tissue by rotating the blade.

5. The apparatus of claim 1 wherein the active leading edge and the terminal end comprise an active cutting and cauterizing element.

6. The apparatus of claim 5 wherein the active cutting and cauterizing element is comprised of an ultrasonic element.

7. The apparatus of claim 5 wherein the active cutting and cauterizing element is comprised of an inductively-heated ferromagnetic element.

8. The apparatus of claim 5 wherein the active cutting and cauterizing element is comprised of an electro-cautery element.

9. An endoscopic vessel harvester, comprising:
   a longitudinal rod having a handle at a first end and terminating at a tapered dissector tip at a second distal end adapted to be inserted into a body of a patient having a target vessel to be removed from the body, wherein the dissector tip is configured to be manually guided into tissue of the body along an anterior side of the target vessel so that an amount of connective tissue of the body is maintained between the dissector tip and the target vessel; and
   a ring-shaped blade mounted to the rod and positionable in a plane substantially perpendicular to a longitudinal direction of the rod and proximal of the dissector tip, wherein the blade forms a lateral loop having a partial ring with a terminal end, wherein the blade and rod have a first configuration in which the terminal end pierces tissue around the vessel in order to center the vessel and a surrounding pedicle within the blade without cutting the vessel, wherein the blade and rod have a second configuration in which the terminal end fits within a profile of the rod so that the partial ring and the rod completely encircle at least a portion of the target vessel and a pedicle of tissue surrounding the target vessel, wherein the blade comprises an active leading edge configured to make a vasiform cut centered around the target vessel and the surrounding pedicle and to simultaneously cauterize side branches of the target vessel as the rod advances and the vessel remains unsevered while the vasiform cut is made.

10. The harvester of claim 9 wherein the blade is rotationally mounted to the rod for pivoting between a retracted position and an extended position.

11. The harvester of claim 9 further comprising a signal conductor passing through the rod and blade for coupling an alternating signal from a generator to the active leading edge.

12. The harvester of claim 9 wherein a gap in the partial ring adjacent the terminal end provides entry into the partial ring while in the first configuration, and wherein the terminal end pierces the tissue by rotating the blade.

13. The harvester of claim 9 wherein the active leading edge and the terminal end comprise an active cutting and cauterizing element.

14. The harvester of claim 13 wherein the active cutting and cauterizing element is comprised of an ultrasonic element.

15. The harvester of claim 13 wherein the active cutting and cauterizing element is comprised of an inductively-heated ferromagnetic element.

16. The harvester of claim 13 wherein the active cutting and cauterizing element is comprised of an electro-cautery element.

* * * * *